United States Patent
Vinther et al.

(10) Patent No.: US 9,187,547 B2
(45) Date of Patent: Nov. 17, 2015

(54) HUMAN INSULIN ANALOGUES AND DERIVATIVES COMPRISING CYSTEINE SUBSTITUTIONS

(75) Inventors: Tine Nygaard Vinther, Frederiksberg C (DK); Thomas Boerglum Kjeldsen, Virum (DK); Frantisek Hubalek, Herlev (DK); Knud J. Jensen, Copenhagen N (DK)

(73) Assignee: Novo Nordisk A/S, Bagsvaerd (DK)

( * ) Notice: Subject to any disclaimer, the term of this patent is extended or adjusted under 35 U.S.C. 154(b) by 24 days.

(21) Appl. No.: 14/004,532

(22) PCT Filed: Mar. 15, 2012

(86) PCT No.: PCT/EP2012/054504
§ 371 (c)(1),
(2), (4) Date: Oct. 18, 2013

(87) PCT Pub. No.: WO2012/123519
PCT Pub. Date: Sep. 20, 2012

(65) Prior Publication Data
US 2014/0031279 A1    Jan. 30, 2014

Related U.S. Application Data

(60) Provisional application No. 61/466,578, filed on Mar. 23, 2011.

(30) Foreign Application Priority Data

Mar. 15, 2011  (EP) ..................................... 11158315

(51) Int. Cl.
*C07K 14/62* (2006.01)
*A61K 38/28* (2006.01)
*A61K 38/00* (2006.01)

(52) U.S. Cl.
CPC .................. *C07K 14/62* (2013.01); *A61K 38/28* (2013.01); *A61K 38/00* (2013.01)

(58) Field of Classification Search
CPC ................................ A61K 38/28; C07K 14/62
See application file for complete search history.

(56) References Cited

U.S. PATENT DOCUMENTS

| | | | | |
|---|---|---|---|---|
| 5,491,216 A | * | 2/1996 | Hoffmann et al. | 530/303 |
| 5,766,897 A | * | 6/1998 | Braxton | 435/463 |
| 8,815,798 B2 | * | 8/2014 | Ludvigsen et al. | 514/5.9 |
| 8,853,155 B2 | * | 10/2014 | Madsen et al. | 514/5.9 |
| 8,883,722 B2 | * | 11/2014 | Hubalek et al. | 514/5.9 |
| 2007/0049688 A1 | | 3/2007 | Kozlowski et al. | |
| 2013/0157938 A1 | * | 6/2013 | Madsen et al. | 514/5.9 |

FOREIGN PATENT DOCUMENTS

| | | |
|---|---|---|
| CN | 102933599 A | 2/2013 |
| EP | 214826 A2 | 3/1987 |
| EP | 2017288 A1 | 1/2009 |
| WO | 90/01038 A1 | 2/1990 |
| WO | 92/00321 A1 | 1/1992 |
| WO | 00/69901 A2 | 11/2000 |
| WO | 02/094200 | 11/2002 |
| WO | 2004/060965 A2 | 7/2004 |
| WO | 2004/060966 A2 | 7/2004 |
| WO | 2005/056636 A2 | 6/2005 |
| WO | 2009/067636 A2 | 5/2009 |
| WO | 2010/033220 A2 | 3/2010 |
| WO | 2010/080609 A1 | 7/2010 |
| WO | WO 2010/080606 A1 * | 7/2010 |

OTHER PUBLICATIONS

Brewer C F et al., Analytical Biochemistry, "Evidence for Possible Nonspecific Reactions Between N-Ethylmaleimide and Proteins", 1967, vol. 18, pp. 248-255.
Goodson R J et al., Biotechnology, "Site-Directed Pegylation of Recombinant Interleukin-2 At Its Glycosylation Site ", 1990, vol. 8, No. 4, pp. 343-346.
Gorin G et al., Archives of Biochemistry and Biophysics, "Kinetics of the Reaction of N-Ethylmaleimide With Cysteine and Some Congeners", 1966, vol. 115, pp. 593-597.
Hinds K D et al., Advanced Drug Delivery Reviews, "Effects of PEG Conjugation on Insulin Properties ", 2002, vol. 54, pp. 505-530.
Kurtzhals P et al., Journal of Biochemistry, "Albumin Binding of Insulins Acylated With Fatty Acids: Characterization of the Ligand-Protein Interaction and Correlation Between Binding Affinity and Timing of the Insulin Effect in Vivo.; ", 1995, vol. 312, pp. 725-731.
Smyth D G et al., Biochemical Journal, "Reactions of N-Ethylmaleimide With Peptides and Amino Acids", 1964, vol. 91, pp. 589-595.
Zeng Z H et al., Biochimica ET Biophysica ACTA, "Conformational Correlation and Coupled Motion Between Residue A21 and B25 Side Chain Observed in Crystal Structures of Insulin Mutants At Position A21; ", 2000, vol. 1479, No. 1-2, pp. 225-236.

* cited by examiner

*Primary Examiner* — Christina Bradley
(74) *Attorney, Agent, or Firm* — Richard W. Bork

(57) ABSTRACT

The present invention relates to human insulin analogues containing a substituting cysteine, to human insulin derivatives containing a PEGylated substituting cysteine and methods of making such. The compounds of the invention may be useful for the treatment of diabetes.

14 Claims, 5 Drawing Sheets

SEQUENCE LISTING

```
<160> NUMBER OF SEQ ID NOS: 18

<210> SEQ ID NO 1
<211> LENGTH: 21
<212> TYPE: PRT
<213> ORGANISM: Artificial
<220> FEATURE:
<223> OTHER INFORMATION: A-chain of A21C, desB30 human insulin

<400> SEQUENCE: 1

Gly Ile Val Glu Gln Cys Cys Thr Ser Ile Cys Ser Leu Tyr Gln Leu
1               5                   10                  15

Glu Asn Tyr Cys Cys
            20

<210> SEQ ID NO 2
<211> LENGTH: 29
<212> TYPE: PRT
<213> ORGANISM: Artificial
<220> FEATURE:
<223> OTHER INFORMATION: B-chain of A21C, desB30 human insulin

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
```

<210> SEQ ID NO 3
<211> LENGTH: 21
<212> TYPE: PRT
<213> ORGANISM: Artificial
<220> FEATURE:
<223> OTHER INFORMATION: A-chain of B25C, desB30 human insulin

<400> SEQUENCE: 3

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 4
<211> LENGTH: 29
<212> TYPE: PRT
<213> ORGANISM: Artificial
<220> FEATURE:
<223> OTHER INFORMATION: B-chain of B25C, desB30 human insulin

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Cys Tyr Thr Pro Lys
            20                  25

<210> SEQ ID NO 5
<211> LENGTH: 21
<212> TYPE: PRT
<213> ORGANISM: Artificial
<220> FEATURE:
<223> OTHER INFORMATION: A-chain of A10C, desB30 human insulin

<400> SEQUENCE: 5

Gly Ile Val Glu Gln Cys Cys Thr Ser Cys Cys Ser Leu Tyr Gln Leu
1               5                   10                  15

Glu Asn Tyr Cys Asn
            20

<210> SEQ ID NO 6
<211> LENGTH: 29
<212> TYPE: PRT
<213> ORGANISM: Artificial
<220> FEATURE:
<223> OTHER INFORMATION: B-chain of A10C, desB30 human insulin

<400> SEQUENCE: 6

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 7
<211> LENGTH: 21
<212> TYPE: PRT
<213> ORGANISM: Artificial
<220> FEATURE:
<223> OTHER INFORMATION: A-chain of A14C, desB30 human insulin

<400> SEQUENCE: 7

Gly Ile Val Glu Gln Cys Cys Thr Ser Ile Cys Ser Leu Cys Gln Leu
1               5                   10                  15

Glu Asn Tyr Cys Asn
            20

<210> SEQ ID NO 8
<211> LENGTH: 29
<212> TYPE: PRT
<213> ORGANISM: Artificial
<220> FEATURE:
<223> OTHER INFORMATION: B-chain of A14C, desB30 human insulin

<400> SEQUENCE: 8

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 9
<211> LENGTH: 21
<212> TYPE: PRT
<213> ORGANISM: Artificial
<220> FEATURE:
<223> OTHER INFORMATION: A-chain of A15C, desB30 human insulin

<400> SEQUENCE: 9

Gly Ile Val Glu Gln Cys Cys Thr Ser Ile Cys Ser Leu Tyr Cys Leu
1               5                   10                  15

Glu Asn Tyr Cys Asn
            20

<210> SEQ ID NO 10
<211> LENGTH: 29
<212> TYPE: PRT
<213> ORGANISM: Artificial
<220> FEATURE:
<223> OTHER INFORMATION: B-chain of A15C, desB30 human insulin

<400> SEQUENCE: 10

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 11
<211> LENGTH: 21
<212> TYPE: PRT
<213> ORGANISM: Artificial
<220> FEATURE:
<223> OTHER INFORMATION: A-chain of A18C, desB30 human insulin

<400> SEQUENCE: 11

Gly Ile Val Glu Gln Cys Cys Thr Ser Ile Cys Ser Leu Tyr Gln Leu
1               5                   10                  15

Glu Cys Tyr Cys Asn
            20

<210> SEQ ID NO 12
<211> LENGTH: 29
<212> TYPE: PRT
<213> ORGANISM: Artificial
<220> FEATURE:
<223> OTHER INFORMATION: B-chain of A18C, desB30 human insulin

<400> SEQUENCE: 12

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 13
<211> LENGTH: 21
<212> TYPE: PRT
<213> ORGANISM: Artificial
<220> FEATURE:
<223> OTHER INFORMATION: A-chain of A19C, desB30 human insulin

<400> SEQUENCE: 13

Gly Ile Val Glu Gln Cys Cys Thr Ser Ile Cys Ser Leu Tyr Gln Leu
1               5                   10                  15

Glu Asn Cys Cys Asn
            20

<210> SEQ ID NO 14
<211> LENGTH: 29
<212> TYPE: PRT
<213> ORGANISM: Artificial
<220> FEATURE:
<223> OTHER INFORMATION: B-chain of A19C, desB30 human insulin

<400> SEQUENCE: 14

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 15
<211> LENGTH: 21
<212> TYPE: PRT
<213> ORGANISM: Artificial
<220> FEATURE:
<223> OTHER INFORMATION: A-chain of B25C, desB30 human insulin

<400> SEQUENCE: 15

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 16
<211> LENGTH: 29
<212> TYPE: PRT
<213> ORGANISM: Artificial
<220> FEATURE:
<223> OTHER INFORMATION: B-chain of B25C, desB30 human insulin

<400> SEQUENCE: 16

Phe Val Asn Gln His Leu Cys Gly Ser His Leu Val Glu Ala Leu Tyr
1               5                   10                  15

Leu Val Cys Gly Glu Arg Gly Phe Cys Tyr Thr Pro Lys
            20                  25

<210> SEQ ID NO 17
<211> LENGTH: 21
<212> TYPE: PRT
<213> ORGANISM: Artificial
<220> FEATURE:
<223> OTHER INFORMATION: A-chain of B27C, desB30 human insulin

<400> SEQUENCE: 17

Gly Ile Val Glu Gln Cys Cys Thr Ser Ile Cys Ser Leu Tyr Gln Leu

```
1               5                  10                 15
Glu Asn Tyr Cys Asn
                20

<210> SEQ ID NO 18
<211> LENGTH: 29
<212> TYPE: PRT
<213> ORGANISM: Artificial
<220> FEATURE:
<223> OTHER INFORMATION: B-chain of B27C, desB30 human insulin

<400> SEQUENCE: 18

Phe Val Asn Gln His Leu Cys Gly Ser His Leu Val Glu Ala Leu Tyr
1               5                  10                 15

Leu Val Cys Gly Glu Arg Gly Phe Phe Tyr Cys Pro Lys
                20                 25
```

HUMAN INSULIN ANALOGUES AND DERIVATIVES COMPRISING CYSTEINE SUBSTITUTIONS

CROSS-REFERENCE TO RELATED APPLICATIONS

This application is a 35 U.S.C. §371 National Stage application of International Application PCT/EP2012/054504 (WO 2012/123519), filed Mar. 15, 2012, which claimed priority of European Patent Application 11158315.9, filed Mar. 15, 2011; this application claims priority under 35 U.S.C. §119 of U.S. Provisional Application 61/466,578; filed Mar. 23, 2011.

TECHNICAL FIELD

The present invention relates to novel human insulin analogues and derivatives. The invention also relates to methods of making such.

INCORPORATION-BY-REFERENCE OF THE SEQUENCE LISTING

The Sequence Listing, entitled "SEQUENCE LISTING", is 6.317 bytes, was created on 1 Mar. 2011 and is incorporated herein by reference.

In accordance with 37 C.F.R. §1.52(e)(5), Applicants enclose herewith the Sequence Listing for the above-captioned application entitled "SEQUENCE LISTING", created on Nov. 28, 2011. The Sequence Listing is made up of 7 kilobytes, and the information contained in the attached "SEQUENCE LISTING" is identical to the information in the specification as originally filed. No new matter is added.

BACKGROUND

Diabetes mellitus is a metabolic disorder in which the ability to utilize glucose is partly or completely lost. Currently, the treatment of diabetes, both type 1 diabetes and type 2 diabetes, relies to an increasing extent on insulin treatment.

Within the last decade a number of human insulin analogues have been designed for particular profiles of action, i.e. fast acting or prolonged action. For instance, insulin Detemir® is a long-acting human insulin analogue for the maintenance of the basal level of insulin. The presence of a fatty acid (myristic acid) covalently bound to the lysine in position B29 delays the action of the insulin.

Despite the recent improvements in insulin analogues available on the market, there is a constant need to enlarge and diversify the existing panel of insulin analogues, exhibiting various pharmacological properties, such as stability and action profiles, while maintaining an efficient insulin activity, in order to fulfil the variety of the specific needs of patients.

Lysine residues have been used as attachment sites for chemical compounds onto insulin molecules. However, the method for preparation of insulin derivatives using lysine as anchoring points presents limitations and is not easy to handle. Indeed, lysine does not allow a site specific attachment onto insulin molecules, as the insulin molecules also comprise two N-terminal α-amino groups that react under similar conditions to ε-amino group of lysine. The reaction with additional chemical groups may result in a heterogenous mixture of one or more of such chemical groups attached at various sites on the insulin. In addition, it is not possible to have an internal lysine in the insulin molecule, when an *A. lyticus* protease (ALP) which cleaves after lysine residues is used in the processing of insulin. Therefore, the attachment site of a chemical group is restricted to lysine residues in the C terminal end of the A-chain and/or the B-chain.

It has been suggested to use cysteine as anchoring point. Kuo et. al. suggest, in the patent document WO2010/033220 related to therapeutic peptides intended for pulmonary administration, to replace any one of the first four amino acids of the B-chain of insulin with a cysteine residue and then to react such cysteine residue with an activated polyethylene glycol (PEG) that is specific for reaction with thiol groups, e.g., a N-maleimidyl polymer. However, it is known that the addition of cystein residues into insulin generally destabilises the molecule, and Kuo et. al. do not disclose a method to prepare such peptides and do not prove the feasibility and the efficiency of such compounds.

Therefore, there is still a need for new insulin analogues and derivatives, new anchoring sites onto insulin molecules, and improved methods for their preparation.

SUMMARY

The invention relates to new insulin analogues and new insulin derivatives.

The invention is based on the recognition that the introduction of an additional cysteine in one of the positions A10C, A14C, A15C, A18C, A19C, A21C, B25C and B27C into the insulin molecule provides a new chemical anchoring point which enables chemoselective reactions.

Surprisingly, it has been found that the insulin analogues of the invention have a good expression rate in host cells, that the additional cysteine does not cause interferences with the existing disulfide bonds in the insulin, and that the insulin derivatives bearing a chemical compound attached to the additional cysteine present a high binding affinity for the insulin receptor and an efficient biological activity.

This is actually of importance because the authors of the present invention have surprisingly found that some cysteine substituted analogues can be prepared and that some of these cysteine substituted analogues can be efficiently or easily used for the attachment of a polymer. The authors of the present invention have faced and overcome several difficulties which go far beyond routine experiments.

In one aspect, the invention relates to a human insulin analogue comprising a human insulin or a desB30 human insulin having one cysteine substitution selected from the group consisting of A10C, A14C, A15C, A18C, A19C, A21C, B25C, B27C.

In another aspect, the invention relates to a human insulin derivative comprising a human insulin analogue as defined herein, wherein the substituting cysteine is covalently attached to a methyl maleimide polyethylene glycol molecule (MM(PEG)) or to a N-ethylmaleimide molecule (NEM).

In one aspect, the novel insulin compounds of the invention provide efficient alternatives to the presently available insulin compounds. Also or alternatively, the novel insulin compounds of the invention can be easily or efficiently prepared. Also or alternatively, the novel insulin compounds of the invention present an efficient binding affinity for the insulin receptor. Also or alternatively, the novel insulin compounds of the invention can be used for the treatment of diabetic patients. Also or alternatively, the novel insulin compounds of the invention present an enhanced stability and/or an extended in vivo half-life in comparison to human insulin. Also or alternatively, the novel insulin compounds of the invention can be administered via subcutaneous route.

In another aspect, the invention relates to the use of human insulin analogues as defined herein as a starting material or intermediate compound for the preparation of a medication. Also or alternatively, the invention relates to the use of human insulin analogues as defined herein as a starting material or intermediate compound for the preparation of or in the process for the preparation of insulin compounds or of human insulin derivatives. The insulin analogues of the invention also offer site specific attachment reactions for the binding of further chemical compounds and the generation of novel insulin derivatives.

In another aspect, the invention relates to methods for the preparation of such human insulin analogues and derivatives. In one aspect, the methods of the invention are simplified compared to those of the prior art and/or easier to handle. Also or alternatively, they are chemoselective. Also or alternatively, they require no protection step of the insulin molecule.

In another aspect, the invention relates to human insulin analogues and derivatives as defined herein for their use as a medication. Also or alternatively, the invention relates to human insulin analogues and derivatives as defined herein for their use in the treatment of diabetes.

In another aspect, the invention relates to a nucleic acid sequence encoding a human insulin analogue as defined herein, or a precursor thereof.

In another aspect, the invention relates to a host cell comprising an expression vector comprising a nucleic acid sequence as defined herein.

BRIEF DESCRIPTION OF DRAWINGS

FIG. 1 *a* concerns analogues with a substituting Cys in the A-chain and FIG. 1 *b* concerns analogues with a substituting Cys in the B-chain.

DESCRIPTION

Figure 1:
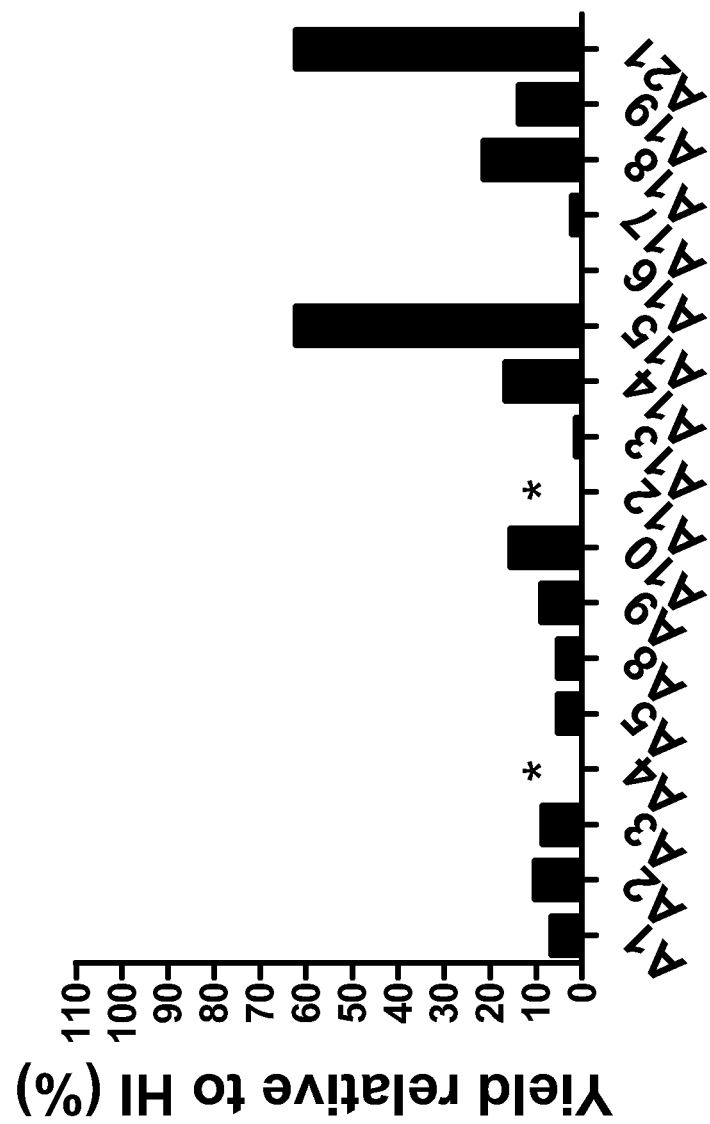
FIG. 1 shows the expression yield of various insulin analogues bearing a substituting Cys.
Figure 1B:
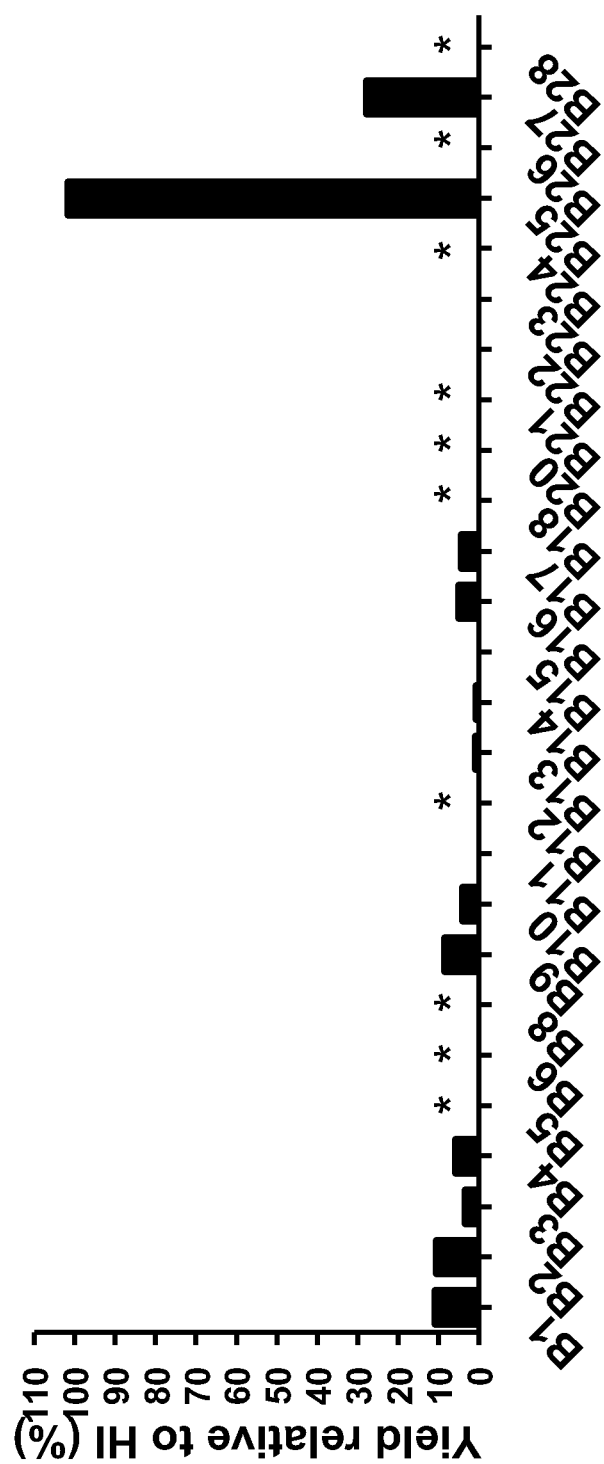

In the present invention novel insulin analogues and derivatives are presented. The novel analogues provide new chemical anchoring points in the view of subsequent chemoselective reactions. The novel insulin analogues and derivatives of the invention can be used for the treatment of diabetes.

In one aspect, the invention relates to a human insulin or a desB30 human insulin having one cysteine substitution selected from the group consisting of A10C, A14C, A15C, A18C, A19C, A21C, B25C, B27C.

The term "human insulin" as used herein means the human insulin hormone whose sequence, structure and properties are well-known. Human insulin has two polypeptide chains, named the A-chain and the B-chain. The A-chain is a 21 amino acid peptide and the B-chain is a 30 amino acid peptide, the two chains being connected by disulphide bridges: a first bridge between the cysteine in position 7 of the A-chain and the cysteine in position 7 of the B-chain, and a second bridge between the cysteine in position 20 of the A-chain and the cysteine in position 19 of the B-chain. A third bridge is present between the cysteines in position 6 and 11 of the A-chain.

The term "desB30 human insulin" as used herein means an analogue of human insulin wherein the B30 amino acid is missing. The sequence of desB30 human insulin is well known. The nucleic acid sequences encoding human insulin and desB30 human insulin are also well known.

Modifications in the insulin molecule are denoted stating the chain (A or B), the position, and the one or three letter code for the amino acid residue substituting the native amino acid residue. Herein terms like "A1", "A2" and "A3" etc. indicate the amino acid in position 1, 2 and 3 etc., respectively, in the A chain of insulin, counted from the N-terminal end of human insulin. Similarly, terms like B1, B2 and B3 etc. indicate the amino acid in position 1, 2 and 3 etc., respectively, in the B chain of insulin, counted from the N-terminal end of human insulin. The numbering of the amino acid positions is based on the native sequence of human insulin. For example, this means that an insulin analog wherein amino acids in position A1 and A2 of the native human insulin sequence are missing starts with amino acid A3. A term like A10C or A10Cys designates that the amino acid in the A10 position has been replaced by a cysteine.

The term "cysteine substitution" as used herein means the replacement of an amino acid residue in a so-called parent insulin molecule with a cysteine amino acid residue. In the broadest scope of the invention, the amino acid residue which is replaced by a cysteine is located in position A10, A14, A15, A18, A19, A21, B25 or B27 on the parent insulin molecule. Said cysteine amino acid residue is named "substituting cysteine" and the resulting insulin molecule is named "substituted insulin" or "insulin analogue" or "human insulin analogue".

In one embodiment, the invention relates to human insulin or a desB30 human insulin thereof having one and only one cysteine substitution, said substitution being selected from the group consisting of A10C, A14C, A15C, A18C, A19C, A21C, B25C, B27C.

In one embodiment of the invention, the cysteine substitution is A21C.

In another embodiment, the three disulfide bonds of human insulin are retained.

Non-limiting examples of substituted insulin according to the invention are A10C human insulin, A14C human insulin, A15C human insulin, A18C human insulin, A19C human insulin, A21C human insulin, B25C human insulin, B27C human insulin, A10C, desB30 human insulin, A14C, desB30 human insulin, A15C, desB30 human insulin, A18C, desB30 human insulin, A19C, desB30 human insulin, A21C, desB30 human insulin, B25C, desB30 human insulin and B27C, desB30 human insulin. Dimers of these compounds are also part of the invention. Dimer of B25C human insulin and dimer of B25C, desB30 human insulin are non-limiting examples of such dimers.

As a non-limiting example, the sequence of A21C, desB30 human insulin (reported as SEQ ID NO 1 for the A-chain and SEQ ID NO 2 for the B-chain in the accompanying sequence listing) is represented by Chem. 1 hereunder:

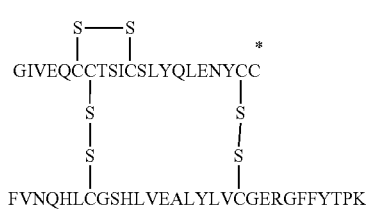

Chem. 1 wherein C* designates the substituting cystein in position A21 and —S—S— indicates disulfide bridges.

The sequence of the other insulin analogues of the invention are defined accordingly.

As a non-limiting example, the sequence of a dimer of B25C, desB30 human insulin (reported as SEQ ID NO 3 for the A-chain and SEQ ID NO 4 for the B-chain in the accompanying sequence listing) is represented by Chem. 2 hereunder:

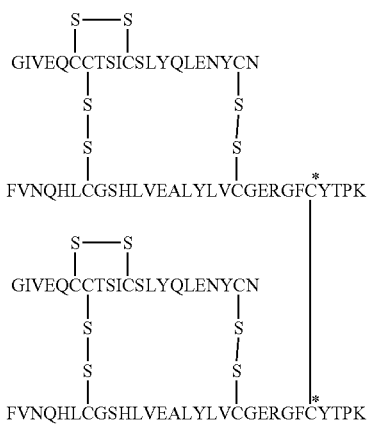

Chem. 2 wherein C* designates the substituting cystein in position B25, —S—S— indicates disulfide bridges and —C*—C*— indicates the dimerization.

As a non-limiting example, the sequence of A10C, desB30 human insulin (reported as SEQ ID NO 5 for the A-chain and SEQ ID NO 6 for the B-chain in the accompanying sequence listing) is represented by Chem. 3 hereunder:

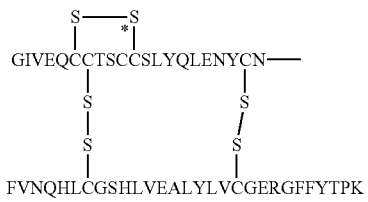

As a non-limiting example, the sequence of A14C, desB30 human insulin (reported as SEQ ID NO 7 for the A-chain and SEQ ID NO 8 for the B-chain in the accompanying sequence listing) is represented by Chem. 4 hereunder:

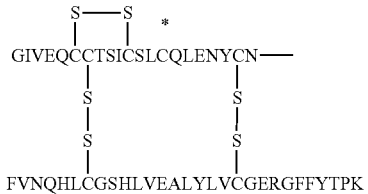

As a non-limiting example, the sequence of A15C, desB30 human insulin (reported as SEQ ID NO 9 for the A-chain and SEQ ID NO 10 for the B-chain in the accompanying sequence listing) is represented by Chem. 5 hereunder:

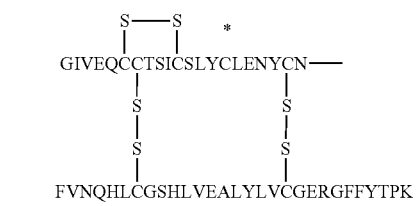

As a non-limiting example, the sequence of A18C, desB30 human insulin (reported as SEQ ID NO 11 for the A-chain and SEQ ID NO 12 for the B-chain in the accompanying sequence listing) is represented by Chem. 6 hereunder:

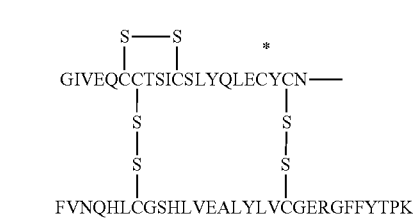

As a non-limiting example, the sequence of A19C, desB30 human insulin (reported as SEQ ID NO 13 for the A-chain and SEQ ID NO 14 for the B-chain in the accompanying sequence listing) is represented by Chem. 7 hereunder:

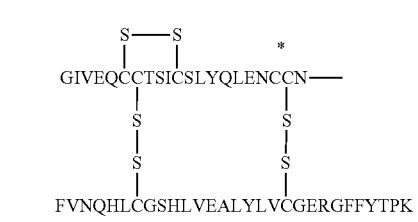

As a non-limiting example, the sequence of B25C, desB30 human insulin (reported as SEQ ID NO 15 for the A-chain and SEQ ID NO 16 for the B-chain in the accompanying sequence listing) is represented by Chem. 8 hereunder:

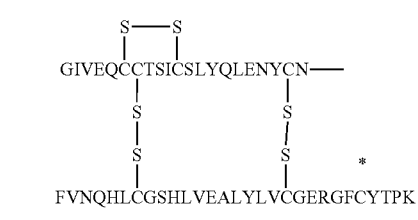

As a non-limiting example, the sequence of B27C, desB30 human insulin (reported as SEQ ID NO 17 for the A-chain and SEQ ID NO 18 for the B-chain in the accompanying sequence listing) is represented by Chem. 9 hereunder:

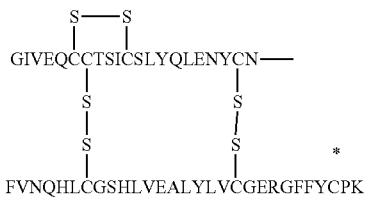

In the chemical formula Chem. 1 to Chem. 9, insulin analogues are shown in a mature form, C* designates the substituting cystein and —S—S— indicates disulfide bridges.

The substituted insulins of the invention present the surprising advantage of a good expression rate in host cells. As shown in FIG. 1, the authors tested the production of a total of 43 substituted insulins in yeast cells, each insulin bearing a different substituting cysteine. Surprisingly, 8 of these insulin analogues were expressed with a satisfactory yield, i.e. with a yield higher than 12.5% relative to human insulin (HI) which renders it possible to further work with these analogues. These 8 insulin analogues, expressed from yeast cells in the form of precursors, had one of the following cystein substitutions: A10C, A14C, A15C, A18C, A19C, A21C, B25C and B27C.

It is another surprising advantage of the substituted insulin of the invention that the additional cysteine does not cause interferences with the existing disulfide bonds in the insulin molecule. This aspect is of particular interest as it allows the use of the substituted insulin of the invention as a starting material or an intermediate compound in order to obtain PEGylated insulin derivatives. Indeed, the substituting cysteine according to the invention is useful as an anchoring point for the selective attachment of a maleimide-polyethylene glycol (PEG) molecule.

In another aspect, the invention relates to a human insulin derivative comprising a substituted insulin as defined above, and wherein the substituting cysteine is further PEGylated.

By "insulin derivative" as used herein is meant substituted insulin as previously disclosed, which is further chemically modified by introducing a PEG side chain or a N-ethylmaleimide (NEM) moiety in one substituting cysteine.

It is herein to be understood that "PEGylation" designates the covalent attachment of a polyethylene glycol (PEG) to another compound, possibly via a linker. The term "PEG" herein designates polyethylene glycol (PEG) or a derivative thereof, eventually coupled to a linker, as known in the art.

In one embodiment, the PEG is defined by the name $PEG_n$ which designates a PEG of the structure represented by Chem. 10:

$$HO—CH2—(CH2—O—CH2—)_n—CH2—OH \quad \text{Chem. 10:}$$

wherein n is an entire number and ranges from 1 to 12. In one embodiment, n ranges from 8 to 12. In another embodiment, n is 12. The short chain (CH2—O—CH2) is also called oligo ethylene glycol (OEG).

In another embodiment, the PEGylation occurs onto the sulfhydryl group of substituting cysteine residue via a linker. The linker may comprise a maleimide moiety. In one embodiment, the polyethylene glycol molecule is or comprises $MM(PEG)_n$ wherein PEG is molecule of Chem. 1, with a maleimide group as a linker and with a methyl group at the free end of the PEG molecule. "n" is an entire number and ranges from 1 to 12, from 8 to 12 or "n" is 12. In one embodiment, the polyethylene glycol molecule is or comprises $MM(PEG)_{12}$ which designates a PEG molecule of Chem. 11:

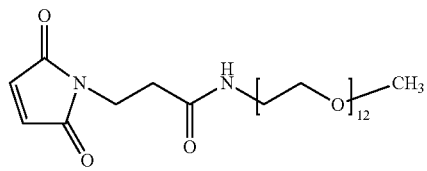

In other words, $MM(PEG)_{12}$ is a PEG molecule of Chem. 10 with n being 12, with a maleimide group as a linker and with a methyl group at the free end of the PEG molecule.

As a non-limiting example, by "A10C-MM(PEG)$_{12}$ human insulin" is meant an insulin derivative wherein the amino acid in position A10 in the naturally occurring human insulin has been replaced by a cysteine, and wherein a $MM(PEG)_{12}$ has been attached to the sulfhydryl group of said cysteine.

In another embodiment, a N-ethylmaleimide (NEM) is covalently attached to the substituting cysteine of substituted insulin of the invention, instead of a $MM(PEG)_n$ molecule. As a non-limiting example, Chem. 12 represents a A21C-NEM desB30 insulin:

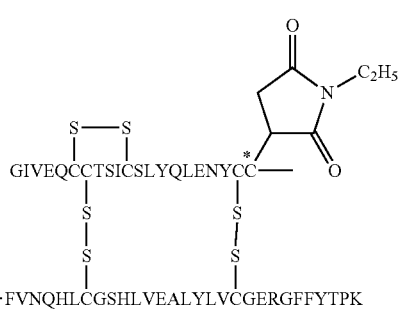

wherein C* designates the substituting cystein in position A21 and —S—S— indicates disulfide bridges.

Non-limiting examples of insulin derivatives according to the invention are A10C-MM(PEG)$_{12}$ human insulin, A14C-MM(PEG)$_{12}$ human insulin, A15C-MM(PEG)$_{12}$ human insulin, A18C-MM(PEG)$_{12}$ human insulin, A19C-MM(PEG)$_{12}$ human insulin, A21C-MM(PEG)$_{12}$ human insulin, B25C-MM(PEG)$_{12}$ human insulin, B27C-MM(PEG)$_{12}$ human insulin, A10C-MM(PEG)$_{12}$ desB30 human insulin, A14C-MM(PEG)$_{12}$ desB30 human insulin, A15C-MM(PEG)$_{12}$ desB30 human insulin, A18C-MM(PEG)$_{12}$ desB30 human insulin, A19C-MM(PEG)$_{12}$ desB30 human insulin, A21C-MM(PEG)$_{12}$ desB30 human insulin, B25C-MM(PEG)$_{12}$ desB30 human insulin and B27C-MM(PEG)$_{12}$ desB30 human insulin, A10C-NEM human insulin, A14C-NEM human insulin, A15C-NEM human insulin, A18C-NEM human insulin, A19C-NEM human insulin, A21C-NEM human insulin, B25C-NEM human insulin, B27C-NEM human insulin, A10C-NEM desB30 human insulin, A14C-NEM desB30 human insulin, A15C-NEM desB30 human insulin, A18C-NEM desB30 human insulin, A19C-NEM desB30 human insulin, A21C-NEM desB30 human insulin, B25C-NEM desB30 human insulin and B27C-NEM desB30 human insulin.

As a non-limiting example, A21C-MM(PEG)$_{12}$ desB30 human insulin, is also named S{Beta-A21}-[1-[3-[2-[2-[2-[2-[2-[2-[2-[2-[2-[2-[2-(2-methoxyethoxy)ethoxy]ethoxy]ethoxy]ethoxy]ethoxy]ethoxy]ethoxy]ethoxy]ethoxy]ethylamino]-3-oxopropyl]-2,5-dioxo pyrrolidin-3-yl]-[CysA21],des-ThrB30-Insulin(human).

The insulin derivatives of the invention represent alternative insulin compounds useful for the treatment of diabetic patients. Indeed, they do present a binding affinity for insulin receptors. In one embodiment, insulin derivatives of the invention present a binding affinity for insulin receptors that is superior to 0% compared to naturally occurring human insulin. In another embodiment, insulin derivatives of the invention present a binding affinity for insulin receptors that is superior to 0.1%. 0.2%. 0.3%. 0.4 or 0.5%. In another embodiment, insulin derivatives of the invention present a binding affinity for insulin receptors that is superior to 1%, 2%, 3%, 4%, 5%, 6%, 8%, 10% or 11% or is of 10% or 11%.

In one embodiment, the invention comprises one enantiomere of a PEGylated insulin derivative. In another embodiment, the invention comprises a mixture of enantiomeres of a PEGylated insulin derivative.

As a non-limiting example, A21C-MM(PEG)$_{12}$ desB30 human insulin is represented in Chem. 13 hereunder:

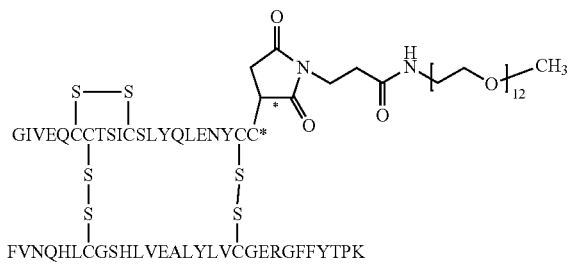

and comprises either the R or the S enantiomers or a mixture of the R and the S enantiomers. Both enantiomers present an efficient binding to insulin receptors. C* designates the substituting cystein in position A21 and —S—S— indicates disulfide bridges.

The substituted insulin analogues of the invention may be prepared using the known techniques in the field of protein engineering, as disclosed in the patent document EP0214826.

In another aspect, the invention relates to a method for producing a precursor of human insulin or desB30 human insulin having one cysteine substitution selected from the group consisting of A10C, A14C, A15C, A18C, A19C, A21C, B25C, B27C.

In one embodiment, said method comprises a step (i) of culturing a host cell comprising a nucleic acid sequence encoding a precursor as defined above.

In one embodiment, the host cell of step (i) is a yeast host cell and in a further embodiment the yeast host cell is selected from the genus *Saccharomyces*. In a further embodiment the yeast host cell is selected from the species *Saccharomyces cerevisiae*. In a further embodiment the yeast host cell is *Saccharomyces cerevisiae* strain MT663.

The host cell may be cultivated according to well known techniques and protocols, such as disclosed in U.S. Pat. No. 6,500,645. The host cell is generally cultivated under appropriate conditions into an appropriate culture medium, and the resulting precursor from step (i) is generally expressed and released by the host cell into the culture medium. The precursor may be further collected from the culture medium, separated, purified and/or concentrated according to known techniques.

In another embodiment, the nucleic acid sequence of step (i) comprises a sequence encoding the naturally occurring insulin or a desB30 human insulin, wherein the codon corresponding to the amino acid in one of the positions A10, A14, A15, A18, A19, A21, B25 and B27 in the resulting precursor has been modified to a codon encoding a cysteine amino acid. In another aspect, the invention relates to the nucleic acid of step (i). The nucleic acid sequence encoding the naturally occurring insulin, the desB30 human insulin and cysteine encoding codons are known in the art.

In another aspect, the invention relates to a vector comprising the nucleic acid sequence of step (i). Vectors are known in the art for various host cells.

The nucleic acid sequence of step (i) and vectors containing such are obtained according to well known techniques in the field of molecular biology. In one embodiment, the cysteine substitution according to the invention is introduced in the insulin coding sequence by overlapping polymerase chain reactions (PCRs).

The vectors containing the nucleic acid of step (i) are chosen according to the host cell to be transformed. Appropriate transformation techniques are also well known in the art.

In another aspect, the invention relates to a host cell containing a nucleic acid sequence of step (i) or a vector comprising the nucleic acid sequence of step (i). Host cell is as defined above.

In another aspect, the invention relates to the precursor obtained from step (i).

In one embodiment, the precursor encoded in step (i) is a proinsulin-like fusion protein which comprises or consists of a spacer followed by the B-chain linked to the A-chain(A1-A21) by a mini C-peptide. In a further embodiment, the spacer comprises or consists of the amino acid sequence EEAEAEAPK, the B-chain is B-chain(B1-B29), the mini C-peptide is of sequence AAK and the A-chain is A-chain (A1-A21).

The term "precursor" as used herein refers to an insulin molecule in a non-mature form. In one embodiment, the term "precursor" refers to an insulin molecule which needs some further processing in order to become mature. The term "mature" as used herein refers to an active form of an insulin molecule. In one embodiment, an insulin precursor comprises a A-chain and a B-chain, wherein the A-chain and the B-chain are linked together not only by disulfide bridges but also by one or several further peptidic sequences. In one embodiment, the insulin precursor is or comprises a so-called proinsulin-like fusion protein consisting of a spacer (EEAEAE-APK) followed by the B-chain (B1-B29), the B-chain being linked to the A-chain(A1-A21) by a mini C-peptide AAK.

The authors of the present invention surprisingly found that the substituted insulins of the invention were efficiently expressed from the host cells. Indeed, a total of 43 nucleic acid sequences have been designed and transformed into yeast cells, encoding 43 possible variants of desB30 human insulin, each bearing one different substituting cysteine. As a result, less than half of the analogues with the modification in the B-chain had an expression yield measurable by reverse-phase high-performance liquid chromatography (RP-HPLC). Although most of the analogues with the cysteine modification in the A-chain were expressed, the yield was generally low for both A- and B-chain. Some analogues could not be detected from a matrix-assisted laser desorption ionisation-time of flight mass spectrometry (MALDI-TOF MS) spectra, indicating that they were either not expressed or had an expression yield below the detection limit: this was the case of the analogues with the cystein substitutions A16C, B11C, B15C, B22C and B23C.

Altogether, 8 analogue precursors were expressed with a satisfactory yield. Said 8 precursors are precursors of the analogues having one of the following cysteine substitutions:

A10C, A14C, A15C, A18C, A19C, A21C, B25C and B27C. In yeast cells, these 8 analogues were expressed with a yield higher than 12.5% relative to human insulin (HI).

Some of the expressed analogue precursors are expressed from step (i) with a proportion of such precursors bearing a modification on the sulfhydryl group of the substituting cysteine. Such modification may be a covalent dimer formation, the attachment of a cysteine moiety, the attachment of a glutathione moiety or another non identified modification. The proportion of such modified precursors relative to the total amount of expressed precursor varies from one analogue to the other. The analogues A18C, A19C and A21C present the highest proportion of non-modified precursors relative to the total amount of expressed precursors. The analogues expressed with higher proportions of modified precursors, for example A10C, A14C, A15C, B25C and B27C, can also be used after a reduction step in order to reduce the proportion of modified precursors.

In another aspect, the invention relates to a method for producing a human insulin or an analogue thereof having a cysteine substitution selected from the group consisting of A10C, A14C, A15C, A18C, A19C, A21C, B25C and B27C. In one embodiment, the invention relates to a method for producing a precursor of a human insulin or a precursor of an analogue thereof having a cysteine substitution selected from the group consisting of A10C, A14C, A15C, A18C, A19C, A21C, B25C and B27C.

In one embodiment, said method comprises the following steps:
(i) culturing a host cell comprising a nucleic acid sequence encoding a precursor for a substituted insulin; and
(ii) converting the precursor into a mature substituted insulin of the invention.

Step (i) and its various embodiments are as disclosed previously.

In one embodiment, the conversion step (ii) is run on the culture medium containing the insulin precursor of step (i). In another embodiment, the conversion step (ii) is run on the culture medium of step (i) after removal of the host cells, e.g. on a cell-free supernatant after centrifugation.

In another embodiment, the conversion step (ii) is preceded by a step of isolating the insulin precursor of step (i) from the culture medium. This may be done according to known techniques.

In another embodiment, the precursor is concentrated, purified or partially purified prior to the conversion step (ii), e.g. by a capture step across a cation exchange column.

The conversion of step (ii) is aimed to convert the insulin precursor of step (i) into mature insulin. Non-limiting examples of conversion methods include enzymatic conversion by means of trypsin or by means of an *Achromobacter lyticus* protease (ALP). In one embodiment, ALP is used in the presence of an L-threonine ester followed by conversion of the threonine ester of the insulin analogue into the insulin analogue by basic or acid hydrolysis as described in U.S. Pat. Nos. 4,343,898 or 4,916,212.

In one embodiment, the precursor of step (i) is converted into mature insulin analogue through digestion with an *Achromobacter lyticus* protease. The ALP enzyme cuts the precursor after lysine residues. As a result, the spacer and C peptide are cut out of the insulin molecule. The A-chain and B-chain are only linked by the disulfide bridges. In the embodiment where the proinsulin-like fusion protein comprises an EEAEAEAPK spacer and an AAK mini C-peptide as previously disclosed, the ALP cuts after the lysine residue of the spacer, the lysine residue of the mini C-peptide and after lysine B29, resulting in a des(B30) substituted insulin. If needed, an amino acid residue can subsequently be added in position B30 according to known methods.

In one embodiment, the conversion step (ii) is operated with an ALP enzyme at a pH ranging from 4 to 10. In another embodiment, it is operated at a pH ranging from 8.5 to 9.5 or 9 to 9.5 as this is the range where ALP presents its optimum digestion activity.

It has been observed that the substituted insulin of the invention is susceptible to disulfide scrambling, i.e. thiol-disulfide exchange between reduced cysteine and disulfide bonds, at high pH ranges, such as pH 9 to 9.5 or around, leading to a certain degree of mispairing of disulfide bonds or a certain degree of degradation. This is due to the presence of the free sulfhydryl group and of the additional cysteine in the insulin. Although it is possible to retrieve a certain percentage of mature insulin analogues when the conversion is performed at the high pH where the ALP shows optimum activity, the authors surprisingly found out a pH range offering an optimum balance between ALP digestion activity and insulin precursor stability. Therefore, in another embodiment of the invention, the conversion step (ii) is operated with the enzyme ALP at a pH ranging from 4 to 8.5, from 4 to 8, from 4 to 7.5, from 4 to 7, from 4.5 to 6.5, from 5 to 6, or at a pH of 5.5. The selected pH ranges according to this particular embodiment ease and optimise the conversion process of step (ii), in the view of this higher sensitivity. It allows the digest to proceed fast enough with an acceptable low loss of analogue with free sulfhydryl group.

In an another aspect, the invention relates to a method for producing a human insulin derivative comprising a human insulin or a desB30 human insulin having a cysteine substitution selected from the group consisting of A10C, A14C, A15C, A18C, A19C, A21C, B25C and B27C, and wherein the substituting cysteine is further PEGylated.

In one embodiment, said method comprises a step of attaching a polyethylene glycol molecule onto a substituting cysteine of a human insulin analogue or a precursor thereof, the human insulin analogue and the precursor being as defined above.

In one embodiment, said method comprises the following steps:
(i) culturing a host cell comprising a nucleic acid sequence encoding a human insulin precursor or a desB30 human insulin precursor;
(ii) converting the insulin precursor of step (i) into a mature insulin; and
(iii) reacting the converted insulin of step (ii) with PEG molecules.

Steps (i) and (ii) and their various embodiments are as disclosed previously.

In step (iii), one linker of PEG molecule reacts with and covalently attaches to the free sulfydryl group of the substituting cysteine of the insulin analogue, leading to a PEGylated derivative of the substituted insulin of step (ii).

The definition and scope of "PEGylation", of the "PEG molecules" and of the linker are as previously defined in relation to the insulin derivatives of the invention.

In one embodiment, the resulting insulin derivative is separated and purified by RP-HPLC. In another embodiment, it is further lyophilized.

In one embodiment, the PEGylation step (iii) follows the conversion step (ii). The PEG molecules are added to and incubated with the insulin analogue of step (ii).

In another embodiment, the PEGylation step precedes the conversion step. Thus, in that embodiment, the method of the invention comprises the following steps:

(i) culturing a host cell comprising a nucleic acid sequence encoding a human insulin precursor or a desB30 human insulin precursor;
(ii) reacting the insulin precursor of step (i) with PEG molecules; and
(iii) converting the PEGylated insulin precursor of step (ii) into a mature insulin derivative. This especially, but not only, concerns the insulin analogues which are very prone to degradation, such as the analogue A19C.

In another embodiment, the PEGylation step and a reduction step are performed in a so-called one-pot reaction. This embodiment applies when the insulin precursor is expressed from step (i) with a proportion of such precursors bearing a modification on the sulfhydryl group of the substituting cysteine. This applies for instance, but not only, to dimers of B25C human insulin analogues, in order to reduce the dimers into monomers.

In one embodiment, the term "one-pot" reaction means that all components of the reaction are added into one same pot, either at the same time or sequentially.

In one embodiment, the reduction and PEGylation one-pot reaction is performed before the conversion of step (iii).

In one embodiment, the reduction and PEGylation one-pot reaction is achieved by mixing the insulin analogues of interest, in the precursor form, with TCEP (Tris(2-carboxyethyl) phosphine) and by further adding the reaction compound to the analogue-TCEP mixture.

In one embodiment, salt is added to the insulin analogue and/or to the TCEP before the insulin analogue is mixed to the TCEP. In one embodiment, the salt is NaOAc (sodium acetate).

In one embodiment, the TCEP is immobilised TCEP and is equilibrated with a buffer before being mixed to the insulin analogue. In one embodiment, the buffer comprises a salt, such as NaOAc.

In one embodiment, the TCEP and the insulin analogue react together and then the reactive compound is added to the mixture and reacts with the insulin analogue. In one embodiment, the reaction with the added reactive compound proceed for 45 minutes.

In one embodiment, the reactive compound is a maleimide associated compound. In one embodiment the reactive maleimide associated compound is either an N-ethylmaleimide (NEM) molecule or an MM(PEG) molecule, the MM(PEG) molecule including MM(PEG)$_n$ as defined above.

The invention covers the following non-limiting embodiments:

Embodiment 1: A human insulin analogue comprising a human insulin or a desB30 human insulin having one cysteine substitution selected from the group consisting of A10C, A14C, A15C, A18C, A19C, A21C, B25C, B27C.

Embodiment 2: A human insulin analogue according to embodiment 1 having one and only one cysteine substitution selected from the group consisting of A10C, A14C, A15C, A18C, A19C, A21C, B25C, B27C.

Embodiment 3: A human insulin analogue according to any of the preceding embodiments, wherein the cysteine substitution is A21C or is B25C.

Embodiment 4: A human insulin analogue according to any of the preceding embodiments, wherein the analogue is or comprises desB30 human insulin.

Embodiment 5: A human insulin analogue selected from the group consisting of A10C human insulin, A14C human insulin, A15C human insulin, A18C human insulin, A19C human insulin, A21C human insulin, B25C human insulin, B27C human insulin, A10C, desB30 human insulin, A14C, desB30 human insulin, A15C, desB30 human insulin, A18C, desB30 human insulin, A19C, desB30 human insulin, A21C, desB30 human insulin, B25C, desB30 human insulin, B27C, desB30 human insulin, a dimer of A10C human insulin, a dimer of A14C human insulin, a dimer of A15C human insulin, a dimer of A18C human insulin, a dimer of A19C human insulin, a dimer of A21C human insulin, a dimer of B25C human insulin, a dimer of B27C human insulin, a dimer of A10C, desB30 human insulin, a dimer of A14C, desB30 human insulin, a dimer of A15C, desB30 human insulin, a dimer of A18C, desB30 human insulin, a dimer of A19C, desB30 human insulin, a dimer of A21C, desB30 human insulin, a dimer of B25C, desB30 human insulin and a dimer of B27C, desB30 human insulin.

Embodiment 6: A human insulin analogue according to any of the preceding embodiments, wherein the analogue is in the form of a precursor.

Embodiment 7: A human insulin analogue of embodiment 6, wherein the precursor form is or comprises a spacer followed by the B-chain (B1-B29), the B-chain being linked to the A-chain (A1-A21) by a mini peptide.

Embodiment 8: A human insulin analogue of embodiment 7, wherein the spacer is of the peptidic sequence EEAEAE-APK and the mini peptide is a mini C-peptide AAK.

Embodiment 9: A human insulin analogue according to any of embodiments 1 to 5, wherein the analogue is in a mature form.

Embodiment 10: A human insulin derivative comprising a human insulin analogue according to any of the preceding embodiments, wherein the substituting cysteine is PEGylated.

Embodiment 11: A human insulin derivative of embodiment 10, wherein a (PEG)$_n$ molecule, with "n" being an entire number between 1 and 12, is covalently attached to the substituting cysteine, via a linker.

Embodiment 12: A human insulin derivative of embodiment 11, wherein "n" is 12 and/or the linker is a maleimide group.

Embodiment 13: A human insulin derivative of embodiment 12 wherein the substituting cysteine is covalently attached to a methyl maleimide polyethylene glycol molecule MM(PEG)$_n$, with "n" being an entire number ranging from 1 to 12, from 8 to 12 or "n" is 12.

Embodiment 14: A human insulin derivative of embodiment 13 selected from the group consisting of A10C-MM(PEG)$_{12}$ human insulin, A14C-MM(PEG)$_{12}$ human insulin, A15C-MM(PEG)$_{12}$ human insulin, A18C-MM(PEG)$_{12}$ human insulin, A19C-MM(PEG)$_{12}$ human insulin, A21C-MM(PEG)$_{12}$ human insulin, B25C-MM(PEG)$_{12}$ human insulin, B27C-MM(PEG)$_{12}$ human insulin, A10C-MM(PEG)$_{12}$ desB30 human insulin, A14C-MM(PEG)$_{12}$ desB30 human insulin, A15C-MM(PEG)$_{12}$ desB30 human insulin, A18C-MM(PEG)$_{12}$ desB30 human insulin, A19C-MM(PEG)$_{12}$ desB30 human insulin, A21C-MM(PEG)$_{12}$ desB30 human insulin, B25C-MM(PEG)$_{12}$ desB30 human insulin and B27C-MM(PEG)$_{12}$ desB30 human insulin.

Embodiment 15: A human insulin derivative comprising a human insulin analogue according to embodiments 1 to 9, wherein the substituting cysteine is covalently attached to a N-ethylmaleimide molecule (NEM).

Embodiment 16: A human insulin derivative of embodiment 15 selected from the group consisting of A10C-NEM human insulin, A14C-NEM human insulin, A15C-NEM human insulin, A18C-NEM human insulin, A19C-NEM human insulin, A21C-NEM human insulin, B25C-NEM human insulin, B27C-NEM human insulin, A10C-NEM desB30 human insulin, A14C-NEM desB30 human insulin, A15C-NEM desB30 human insulin, A18C-NEM desB30 human insulin, A19C-NEM desB30 human insulin, A21C-NEM desB30 human insulin, B25C-NEM desB30 human insulin and B27C-NEM desB30 human insulin.

Embodiment 17: A human insulin derivative according to any of the embodiments 10 to 16, wherein the derivative is in the form of a precursor.

Embodiment 18: A human insulin derivative of embodiment 16, wherein the precursor form is or comprises a spacer followed by the B-chain (B1-B29), the B-chain being linked to the A-chain (A1-A21) by a mini peptide.

Embodiment 19: A human insulin derivative of embodiment 18, wherein the spacer is of the peptidic sequence EEAE-AEAPK and the mini peptide is a mini C-peptide AAK.

Embodiment 20: A human insulin derivative according to any of the embodiments 10 to 16, wherein the derivative is in a mature form.

Embodiment 21: A human insulin derivative according to any of embodiments 10 to 12, wherein the derivative is selected from the group consisting of A21C human insulin or A21C, desB30 human insulin, said insulins being PEGylated on the substituting cysteine.

Embodiment 22: A human insulin derivative according to any of embodiments 10 to 14 and 17 to 21, wherein the derivative is selected from the group consisting of A21C-MM(PEG)$_{12}$ human insulin, A21C-MM(PEG)$_{12}$ desB30 human insulin, a precursor of A21C-MM(PEG)$_{12}$ human insulin, a precursor of A21C-MM(PEG)$_{12}$ desB30 human insulin, or a dimer thereof.

Embodiment 23: A human insulin derivative according to any of embodiments 10 to 14 and 17 to 21, wherein the derivative is selected from the group consisting of B25C-MM(PEG)$_{12}$ human insulin, B25C-MM(PEG)$_{12}$ desB30 human insulin, a precursor of B25C-MM(PEG)$_{12}$ human insulin, a precursor of B25C-MM(PEG)$_{12}$ desB30 human insulin or a dimer thereof.

Embodiment 24: A human insulin derivative according to any of embodiments 22 or 23, in the form of a precursor, wherein the precursor form is or comprises a spacer followed by the B-chain (B1-B29), the B-chain being linked to the A-chain (A1-A21) by a mini peptide.

Embodiment 25: A human insulin derivative of embodiment 24, wherein the spacer is of the peptidic sequence EEAE-AEAPK and the mini peptide is a mini C-peptide AAK.

Embodiment 26: A method of preparing a human insulin analogue, said method comprising a step of culturing a host cell encoding a precursor of a human insulin analogue as defined in embodiments 1 to 8.

Embodiment 27: Method of embodiment 26 wherein the host cell is a yeast cell.

Embodiment 28: Method of embodiment 26 or 27, further comprising a step of converting the precursor into a mature human insulin analogue.

Embodiment 29: Method of embodiment 28 wherein the conversion step is operated with an *Achromobacter lyticus* protease.

Embodiment 30: Method of embodiment 29 wherein the conversion step is operated with an *Achromobacter lyticus* protease at a pH ranging from 4 to 10.

Embodiment 31: Method of embodiment 30 wherein the conversion step is operated with an *Achromobacter lyticus* protease at a pH ranging from 8.5 to 9.5 or 9 to 9.5.

Embodiment 32: Method of embodiment 30 wherein the conversion step is operated with an *Achromobacter lyticus* protease at a pH ranging from 4 to 8.5, from 4 to 8, from 4 to 7.5, from 4 to 7, from 4.5 to 6.5, from 5 to 6, or at a pH of 5.5.

Embodiment 33: Method of preparing a human insulin derivative, said method comprising a step of attaching a polyethylene glycol molecule onto a substituting cysteine of a human insulin analogue as defined in any of embodiments 1 to 9.

Embodiment 34: Method of preparing a human insulin derivative, said method comprising a step of attaching a polyethylene glycol molecule via a linker, or a NEM compound, onto a substituting cysteine of a human insulin analogue as defined in any of embodiments 1 to 9.

Embodiment 35: Method according to embodiment 34 wherein the polyethylene glycol molecule is a MM(PEG)$_n$ molecule, with "n" being an entire number from 1 to 12, from 1 to 8 or "n" being 12.

Embodiment 36: Method according to any of embodiments 33 to 35, wherein the attachment is carried out onto a precursor of a human insulin analogue.

Embodiment 37: Method according to any of embodiments 33 to 35, wherein the attachment is carried out onto a mature human insulin analogue.

Embodiment 38: Method according to embodiment 37, wherein the human insulin analogue is A19C human insulin or A19C, desB30 human insulin.

Embodiment 39: Method according to any of embodiments 33 to 38, wherein the PEGylation step and a reduction step are performed in a so-called one-pot reaction.

Embodiment 40: Method according to embodiment 39 wherein the human insulin analogue bears a modification on the sulfhydryl group of the substituting cysteine.

Embodiment 41: Method according to embodiment 40 wherein the modification on the sulfhydryl group of the substituting cysteine is a gluthationylation, a cysteinylation, an alkylation or a dimerisation, or wherein the human insulin analogue is a dimer of B25C human insulin or a dimer of B25C, desB30 human insulin.

Embodiment 42: Method according to any of embodiments 39 to 41 wherein the reduction and PEGylation one-pot reaction is performed on a precursor of the human insulin analogue.

Embodiment 43: Method according to any of embodiments 39 to 42 wherein the reduction and PEGylation one-pot reaction is achieved by mixing the insulin analogue, preferably in a precursor form, with TCEP (Tris(2-carboxyethyl)phosphine) and by further adding a PEG compound to the analogue-TCEP mixture.

Embodiment 44: Method according to embodiment 43 wherein salt is added to the insulin analogue and/or to the TCEP before the insulin analogue is mixed to the TCEP.

Embodiment 45: Method according to embodiment 44 wherein the salt is NaOAC (sodium acetate).

Embodiment 46: Method according to any of embodiments 43 to 45 wherein the TCEP is immobilised TCEP and is equilibrated with a buffer before being mixed to the insulin analogue.

Embodiment 47: Method according to embodiment 46 wherein the buffer comprises a salt, such as sodium acetate.

Embodiment 48: Method according to any of embodiments 43 to 47 wherein the TCEP and the insulin analogue react together and then a PEG compound is added to the mixture.

Embodiment 49: Method according to any of embodiments 43 to 48 wherein the reaction with the added PEG compound proceeds for 45 minutes.

Embodiment 50: Method according to any of embodiments 43 to 49 wherein the PEG compound is a maleimide associated compound.

Embodiment 51: Method according to any of embodiments 43 to 50 wherein the PEG compound is a MM-PEG molecule, or a MM(PEG)$_n$ molecule with "n" being an entire number from 1 to 12, from 1 to 8 or "n" being 12

Embodiment 52: Method according to any of embodiments 43 to 50 wherein a N-ethylmaleimide (NEM) molecule is used instead of a PEG compound.

Embodiment 53: A nucleic acid sequence encoding a human insulin analogue according to any of embodiments 1 to 8.

Embodiment 54: Use of a human insulin analogue according to any of embodiments 1 to 9 as a starting material or intermediate compound in the process for the preparation of a medication.

Embodiment 55: Use of a human insulin analogue according to any of embodiments 1 to 9 as a starting material or intermediate compound in the process for the preparation of a novel insulin derivative.

Embodiment 56: Use of a human insulin analogue according to any of embodiments 1 to 9 for the binding of a further chemical compound, such as a PEG compound or a NEM molecule, onto the substituting cysteine of said human insulin analogue.

Embodiment 57: Use of a human insulin analogue according to any of embodiments 1 to 9 in the process for the preparation of a human insulin derivative, and especially of a human insulin derivative as defined in any of embodiments 10 to 25.

Embodiment 58: A human insulin analogue of any one of embodiments 1 to 9 or a human insulin derivative of any one of embodiments 10 to 25 for its use as a medication.

Embodiment 59: A human insulin analogue of any one of embodiments 1 to 9 or a human insulin derivative of any one of embodiments 10 to 25 for its use in the treatment of diabetes. Embodiment the invention relates to a nucleic acid sequence encoding a human insulin analogue as defined herein, or a precursor thereof.

Embodiment 60: A host cell encoding a precursor of a human insulin analogue as defined in embodiments 1 to 8.

The invention may also solve further problems that will be apparent from the disclosure of the exemplary embodiments.

EXAMPLES (a) Construction of Plasmids and Expression

A systematic cysteine scan of insulin was performed introducing single mutation on all positions in desB30 insulin with a total of 43 possible insulin variants excluding B29Lys, to be used in later processing. The mutations were introduced in the insulin coding sequence by overlapping polymerase chain reactions (PCRs), according to well known techniques. Material, vectors, strains and construction was as previously described (Kjeldsen et al., 1999; Kjeldsen et al., 1996; Kristensen et al., 1997).

The insulin precursors were expressed in *Saccharomyces cerevisiae* strain MT663 as proinsulin-like fusion proteins consisting of a spacer (EEAEAEAPK) followed by the B-chain(B1-B29) linked to the A-chain(A1-A21) by a mini C-peptide AAK. The precursors were expressed in 5 ml cultures. The culture medium and conditions are as known in the art.

The expression yield for each insulin precursor was determined by reverse-phase high-performance liquid chromatography (RP-HPLC) based on peak area using human insulin (HI) as external standard. The results are reported in FIG. 1 (FIG. 1). The graph of FIG. 1 represents the expression yield, as a percentage of human insulin expression level, for each insulin precursor of analogues bearing a substituting Cys. FIG. 1 *a* concerns the analogues with a substituting Cys in the A-chain and FIG. 1 *b* concerns the analogues with a substituting Cys in the B-chain. The x-axis indicates the substituting position for each insulin analogue (A1, A2, A3, B1, B2 etc) and the y-axis indicates the expression yield.

These results show that the majority of the analogues with the Cys introduced in the A-chain (FIG. 1 *a*) were expressed and almost half of the analogues with the modification in the B-chain (FIG. 1 *b*) had a yield measurable by RP-HPLC. In total about 60% of the constructed analogues were expressed despite the high chance of disulfide scrambling between the 7$^{th}$ introduced Cys and the three existing disulfide bonds. Analogues indicated with a star presented low expression yields and have only been detected by MALDI MS but not by HPLC. Of the 60% expressed a total of 8 analogues (A10C, A14C, A15C, A18C, A19C, A21C, B25C and B27C) had a yield exceeding that of 12.5% relative to HI making them candidates for PEGylation.

(b) Selection of Suitable Analogues for PEGylation

The analogues A10C, desB30, A14C, desB30, A15C, desB30, A18C, desB30, A19C, desB30, A21C, desB30, B25C, desB30 and B27C, desB30 were selected for further analysis of the distribution of modified precursors among the total of expressed precursors.

Therefore, insulin analogues A10C, desB30 human insulin, A14C, desB30 human insulin, A15C, desB30 human insulin, A18C, desB30 human insulin, A19C, desB30 human insulin, A21C, desB30 human insulin, B25C, desB30 human insulin and B27C, desB30 human insulin according to the invention were fermented in Yeast Extract Peptone Dextrose (YPD) media in small 200 ml cultures in duplicates (A10C, A14C, A15C, A18C, A19C and B25C) and triplicates (A21C and B27C) treated equally. The cells were removed by centrifugation and decantation, and the supernatants were acidified to a pH of 3 or just below 3. The precursors were partially purified and concentrated by a capture step across a cation exchange column.

The analogues were analysed by LC/MS (Liquid chromatography/Mass Spectrometry) and the relative amount of each form of precursors was calculated based on areas in the 214 nm ultraviolet (UV) trace, according to known techniques.

Figure 2:
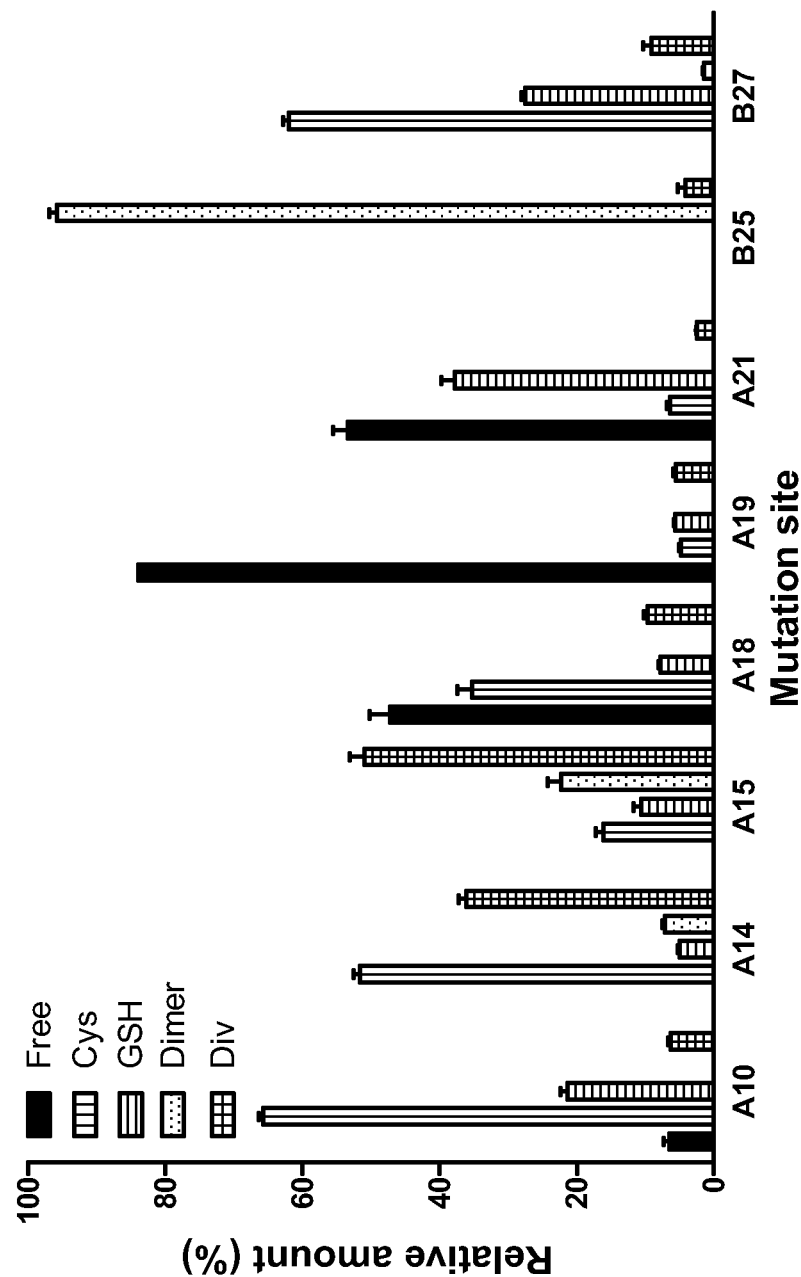
FIG. 2 shows, for various insulin analogues, the proportion of modified precursors relatively to the total amount of expressed analogues precursors.

The results are reported on FIG. 2 (FIG. 2). The graph of FIG. 2 represents, for each of the tested analogues—Cys substitution position indicated along the x-axis—the proportion of various modified precursor as a percentage of the total of expressed analogues (y-axis). The black bars represent the unmodified precursors, also called free precursors, the white bars with vertical stripes represent the cysteinylated precursors, the white bars with horizontal stripes represent the glutathionylated precursors, the white bars with dots represent the dimers precursors and the squared white bars represent precursors with other unidentified modifications.

FIG. 2 shows that the percentage of modified precursors among the total of expressed precursors and the nature of the modifications vary from one analogue to another. The forms of the precursors vary from unmodified substituting cysteine (i.e. unmodified precursors) up to a mixture of cysteinylated, glutathionylated variants and/or covalent dimers of variants.

FIG. 2 also shows that the analogues A18C, desB30, A19C, desB30 and A21C, desB30 human insulin analogues present the highest proportion of unmodified precursors, above 20%. These analogues allow a direct PEGylation step.

Starting from precursors expressed with smaller proportions of unmodified compounds, the efficiency of further PEGylation may be improved if preceded with a selective reduction step of the disulfide bond involving the 7th cysteine, in order to expose the free sulfhydryl group. The selective reduction can be obtained according to the method reported in example (d).

Due to the high sensitivity of the insulin precursors of the invention to alkaline pH, an optimisation of the pH during ALP cleavage was made and it was concluded that the digest proceeded fast enough with acceptable low loss of derivative with free sulfhydryl at pH 5.5, the pH of the elution buffer used in the ion exchange purification step. It has been observed that the precursor A19C was unstable at this pH, leading to significant degradation. Selecting this analogue for alkylation therefore makes it preferable to perform the alkylation reaction prior to ALP digestion.

Based on the expression yield of unmodified derivative and degradation stability, A21C, desB30 insulin analogue, was a good candidate for further PEGylation study, as well as A18C, desB30 and A19C, desB30 analogues. The A100, A140, A150, B25C and B27C, desB30 analogues are also good candidates for further PEGylation with a reduction step.

(c) Purification and PEGylation

The insulin analogue A21C, desB30 human insulin was fermented in 3 L culture. The cell-free culture supernatant was acidified to a pH of 3 or just below 3 and the precursor was partially purified and concentrated by a capture step across a cation exchange column. After elution, the analogue was found in a buffer at pH 5.5. The precursor was then converted to a two chain mature A21C, desB30 human insulin by matrix bound ALP and conversion was verified by MALDI-TOF-MS (Matrix assisted laser desorption ionisation time-of-flight mass spectrometry). Following ALP digest, the analogue was PEGylated with a 100 mM aqueous solution of $MM(PEG)_{12}$ in excess, with an $MM(PEG)_{12}$:analogue molar ratio of 1:25, at room temperature during 3 days with mixing. After reaction was complete a sample was analysed by LC/MS.

Figure 3:
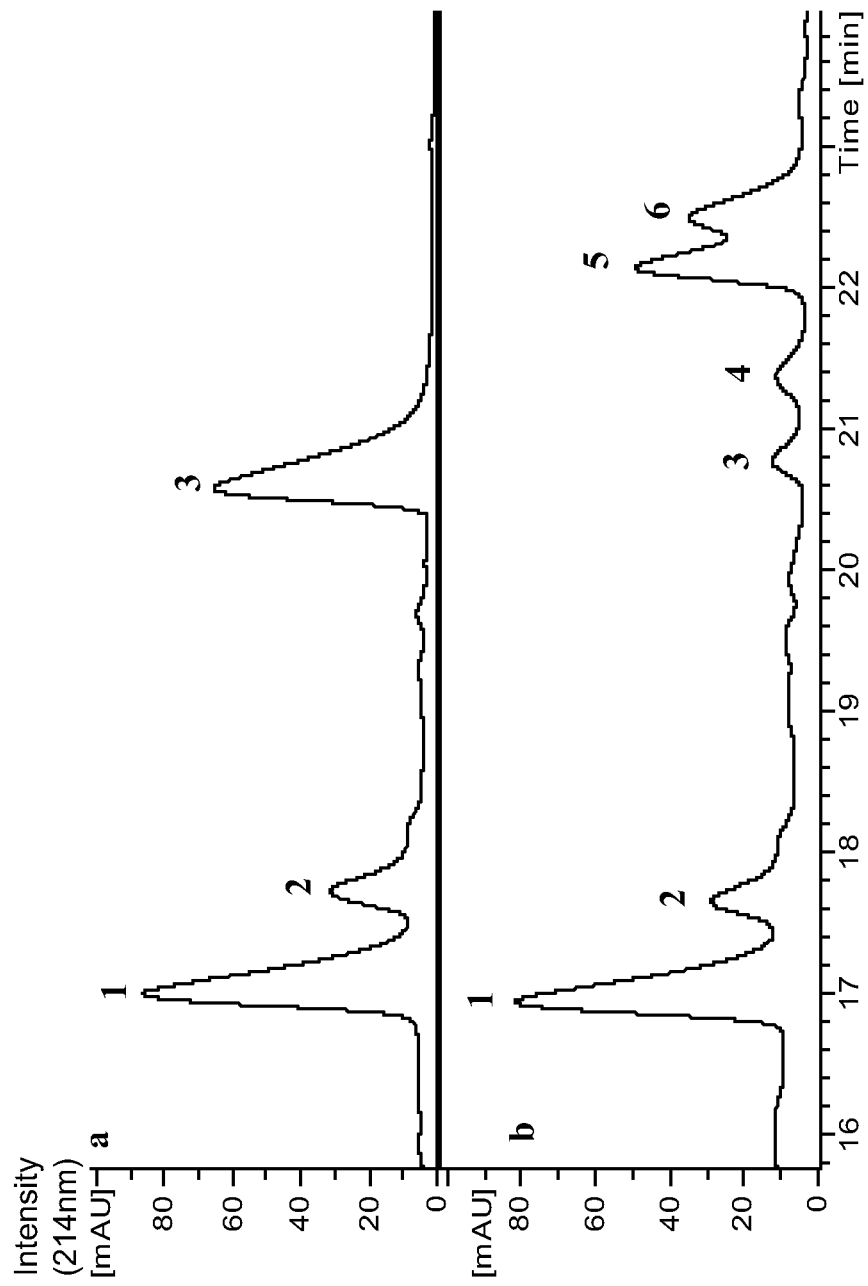
FIG. 3 shows the population of A21CdesB30 analogues and derivatives before (FIG. 3*a*) and after (FIG. 3 *b*) alkylation of A21CdesB30 with MM(PEG)$_{12}$.

FIG. 3 represents a UV chromatogram from the LC/MS run of the A21CDesB30 analogue and derivatives before (FIG. 3 a) and after (FIG. 3 b) alkylation with $MM(PEG)_{12}$, with the intensity of the signals detected from LC/MS being expressed in mAU (milli Absorbance Unit) (y-axis) as a function of time x-axis), in minutes. The peaks corresponding to different derivatives and reagent are following: 1: gluthationylated A21C-PEG, 2: cysteinylated A21C-PEG, 3: unmodified A21C-PEG, 4: reagent, 5: alkylated A21C-PEG1, 6: alkylated A21C-PEG2. PEG1 and PEG2 refer to the 2 enantiomeric forms of the compound. After alkylation, the peak 3 representing the unmodified analogue has diminished and two new peaks 5 and 6 can be seen with higher retention time both with a mass corresponding to the unmodified analogue with a single PEGylation. Comparing before and after reaction with $MM(PEG)_{12}$, it appears that the maleimide compound reacts with the analogue with a free sulfhydryl group. The difference in retention time between peaks 5 and 6 is explained by the presence of two isomeric forms, possibly caused by the formation of a new chiral center at the thioether. A disulfide scrambling between the existing bonds and the $7^{th}$ Cys has been ruled out with V8 enzyme digest analysis together with MS/MS (Tandem mass spectrometry) analyses (data not shown).

The alkylation through Cys chemistry appears to be very chemoselective and close to 100% conversion of derivates with free sulfhydryl was seen.

Directly following alkylation the different derivatives were separated and purified by RP-HPLC using a trifluoroacetic acid (TFA) buffer system. The fractions were lyophilized and the purity was measured by UV 220 nm at neutral and acidic pH.

(d) Reduction and PEGylation in One-Pot Using Immobilized TCEP (Tris(2-carboxyethyl)phosphine)

The PEGylation step is performed together with a reduction step in a so-called one-pot reaction when the insulin precursor is expressed with a proportion of such precursors bearing a modification on the sulfhydryl group of the substituting cystein. This applies for instance with dimers of B25C human insulin analogues, in order to reduce the dimers into monomers.

Precursors of insulin analogues A10C, desB30 human insulin, A14C, desB30 human insulin, A15C, desB30 human insulin, A18C, desB30 human insulin, A19C, desB30 human insulin, A21C, desB30 human insulin, B25C, desB30 human insulin and B27C, desB30 human insulin were prepared and partially purified using cation exchange chromatography as explained in example (b).

TCEP (Tris(2-carboxyethyl)phosphine) immobilized on agarose gel (Thermo Scientific®) was equilibrated in elution buffer (from cation exchange chromatography) mixed 1:1 with 1M NaOAc (sodium acetate) at pH 5.5.

Then, 100 µl TCEP slurry (equilibration buffer removed) was mixed with 30 µl 1M NaOAc pH 5.5 and 25 µl of partially purified analogues precursors as defined above. The samples were mixed by turning in order to suspend the gel for 15 min at room temperature before adding 5µl 10 mM $MM(PEG)_{12}$ (or 100 mM NEM) in water. The samples were then mixed by turning for additionally 45 min at room temperature before adding 60 µl 10% TFA (2,2,2-Trifluoroacetic acid or trifluoro acetic acid) to ensure pH below 3.

During this step, the modified precursors are reduced by the TCEP in order to increase the proportion of unmodified precursors followed by PEGylation in the same pot.

The resulting samples were separated from the TCEP gel by centrifugation and analysed on LC/MS to identify the existence of successfully PEGylated precursors. The retention time and mass are shown in Table 1 for each tested analogue.

The LC method used a Dionex® Ultimate(O)3000 liquid chromatography, 0.05% TFA as buffer A and 0.04% TFA+ 80% acetonitril (w/w) as buffer B, at temperature 60° C. The trap column used was Zorbax® XDB-C18, 3.5 µm, 35×0.3 mm column from Agilent® Technologies and the analytical column used was Zorbax® XDB-C18, 3.5 µm, 150×0.3 mm column from Agilent® Technologies.

The MS method used a LTQ Orbitrap® XL apparatus from ThermoFisher® Scientific, San Jose, Calif.). The mass range selected for the MS was set to 100-2000 m/z (m/z represents the ratio of the mass m and the charge z).

In Table 1 hereunder are reported the elution buffer parameters used for the trap column: the nature of the gradient elution buffer (buffer A with a % of buffer B) (right column), the flow of the elution buffer (in µl/min) (middle column) along time (Retention Time in min.) (left column).

TABLE 1

| Gradient (loading pump) | | |
| --- | --- | --- |
| RT (min) | Flow (µl/min) | % B |
| 0 | 30 | 20 |
| 0 | 30 | 20 |
| 2 | 30 | 27 |

TABLE 1-continued

Gradient (loading pump)

| RT (min) | Flow (µl/min) | % B |
|---|---|---|
| 3 | 30 | 27 |
| 5 | 5 | 20 |

In Table 2 hereunder are reported the elution buffer parameters used for the analysis column: the nature of the gradient elution buffer (buffer A with a % of buffer B) (right column), the flow of the elution buffer (in µl/min) (middle column) along time (Retention Time in min.) (left column).

TABLE 2

Gradient (micro pump)

| RT (min) | Flow (µl/min) | % B |
|---|---|---|
| 0 | 5 | 25 |
| 0 | 5 | 25 |
| 5 | 5 | 25 |
| 35 | 5 | 50 |
| 36 | 5 | 95 |
| 37 | 5 | 92 |
| 38 | 5 | 25 |
| 45 | 5 | 25 |

Table 3 hereunder indicates the timing of valves switching between the two columns, controlling the route for elution buffer through the trap column and analytical column.

TABLE 3

Switch valve

| No. | Time [min] | Valve |
|---|---|---|
| 1 | Initiate | From injector to trap column |
| 2 | 0 | From injector to trap column |
| 3 | 3 | From trap to analytical column |
| 4 | 30 | From injector to trap column |

The results are reported in Table 4 hereunder:

TABLE 4

| Modifying compound: NEM | | Mass (mono isotopic) [Da] | | |
|---|---|---|---|---|
| Mutation site | Analogue | Theoretical | Measured | RT [min] |
| A10C | A10C-NEM | 7024.14768 | 7024.31 | 25.4 |
| A14C | A14C-NEM | 6974.16768 | 6974.36 | 26.5 |
| A15C | A15C-NEM | 7009.17768 | 7009.38 | 31.1 |
| A18C | A18C-NEM | 7023.18768 | 7023.39 | 26.5 |
| A19C | A19C-NEM1 | 6974.16768 | 6974.38 | 27.1 |
| A19C | A19C-NEM2 | 6974.16768 | 6974.39 | 27.6 |
| A21C | A21C-NEM1 | 7023.18768 | 7023.41 | 26.9 |
| A21C | A21C-NEM2 | 7023.18768 | 7023.41 | 27.7 |
| B25C | B25C-NEM | 6990.16768 | 6990.36 | 24.7 |
| B27C | B27C-NEM | 7036.18768 | 7036.39 | 26.8 |

| Modifying compound: MM(PEG)12 | | Mass (mono isotopic) [Da] | | |
|---|---|---|---|---|
| Mutation site | Analogue | Theoretical | Measured | RT [min] |
| A10C | A10C-PEG | 7609.48372 | 7609.71 | 27 |
| A14C | A14C-PEG | 7559.50372 | 7559.78 | 28.1 |
| A15C | A15C-PEG | 7594.51372 | 7594.76 | 32.3 |
| A18C | A18C-PEG1 | 7608.52372 | 7608.78 | 28.2 |
| A18C | A18C-PEG2 | 7608.52372 | 7608.78 | 28.4 |
| A19C | A19C-PEG | 7559.50372 | 7559.74 | 29.4 |

TABLE 4-continued

| A21C | A21C-PEG1 | 7608.52372 | 7608.79 | 28 |
| A21C | A21C-PEG2 | 7608.52372 | 7608.78 | 28.6 |
| B25C | B25C-PEG1 | 7575.50372 | 7575.74 | 26.7 |
| B25C | B25C-PEG2 | 7575.50372 | 7575.74 | 27.2 |
| B27C | B27C-PEG | 7621.52372 | 7621.73 | 28.8 |

This table 4 indicates the theoretical mono isotopic mass in Da for each of the expected analogue precursors compounds in comparison to the measured mono isotopic mass for effectively eluted compounds. The agreement between the theoretical and the measured mass indicates that the reduction-PEGylation reaction has succeeded. The RT indicates the elution time of each compound, i.e. the time when a peak appeared on the UV trace (data not shown). Some of them showed 2 peaks due to chiral center, as has been shown earlier (see FIG. 3) for the A21C compound.

(e) Receptor Binding Assay

To investigate whether the analogues had retained potency after introduction of a Cys and the addition of a PEG chain, an in vitro Insulin receptor (IR) competition binding assay was performed on the A isoform of the insulin receptor, purified from BHK (Baby Hamster Kidney) cells, in a scintillation proximity assay (SPA) as described in the art. The two enantiomeric forms, A21C-PEG1 and A21C-PEG2, of mature PEGylated A21C, desB30 were tested. The two enantiomeric forms of B25C-NEM1 and B25C-NEM2 of mature B25C-NEM desB30 insulin derivatives were also tested. The compounds were obtained as described in example (c), purified on HPLC and freeze-dried).

Binding competition of the insulin analogues and [$^{125}$I] TyrA14-labelled insulin in the SPA assay was used to determine binding receptor affinities. Each plate contained a human insulin (HI) standard (experiment repeated 4 times) and an analogue for testing (experiment repeated 4 times). This was repeated 3 times. The data was analysed according to a four-parameter logistic model as described in the art and the affinities were expressed relative to a human insulin standard as defined by the following mathematical formula:

$$[(IC_{50(insulin)}/IC_{50(analogue)})*100\%].$$  Math. 1:

The results show that A21C-PEG1 and A21C-PEG2 had average relative binding potencies of 10% (±1.7) and 11% (±1.8) respectively with the standard deviation in parentheses. There were no statistical significant differences between the two. The presence of a chiral centre in the linker between the PEG chain and the insulin molecule does not have an effect on the binding properties. Thus, despite the alteration of position A21 from an asparagine to a cysteine residue and the addition of a 12 unit PEG chain the analogue has still retained a fair part of the binding affinities.

The results also show that the B25C-NEM1 and B25C-NEM2 desB30 insulin derivatives had a relative binding potency of 0.24% relative to HI. Thus, despite the alteration on the insulin derivative, it has still retained a part of its binding affinities.

(f) Metabolic Potency Determination

To investigate whether the two stereo isomers A21C-PEG1 and A21C-PEG2 were equally able to generate a response in vitro their metabolic potency were determined by lipogenesis according to known techniques. The compounds were obtained as mentioned in example (c).

Therefore, isolated primary rat adipocytes from SPRD rats were used. The fat pads were removed and placed in degradation buffer containing Hepes buffer, Krebs buffer, 0.1% HSA (human serum albumin), collagenase and glucose. The cells were shaken vigorously for 1 h at 37° C. and the cell suspension were filtered, washed twice and resuspended in incubation buffer containing Hepes buffer, Krebs buffer and 0.1% HSA. Aliquots of 100 µL were distributed in 96-well PicoPlates and incubated 2 h at 37° C. with gentle shaking together with 10 µL glucose solution containing D-[3-$^3$H] glucose and glucose and 10 µL of increasing concentration of human insulin (for reference) or A21C-MM(PEG$_{12}$) insulin analogue, one or the other enantiomeric form. The incubation was stopped with addition of 150 µL MicroScint®E (Packard®) and the amount of incorporated radioactivity was counted for each plate in a TopCount® NXT (PerkinElmer® Life Science).

The data were analysed according to a four-parameter logistic model and the affinities were expressed relative to a human insulin standard as defined by the mathematical formula Math. 1 (see example (e)). Both forms generated a response reflecting their receptor affinities with 7.57% (±2.0) and 10.32% (±3.2) for A21C-PEG1 and A21C-PEG2 respectively and no statistical significant difference were evident between the two.

(g) In Vivo Effect of A21C-MM(PEG$_{12}$) desB30, Human Insulin in Wistar Rats

One of the isomers, A21C-PEG1, was tested in vivo, to investigate its ability to lower glucose in the blood. The analogue was compared to human insulin in two doses administered intravenously in Wistar rats.

Therefore, twenty-nine male, fed Wistar rats (253-319 g) were anesthetized using Hypnorm-Dormicum (0.081 mg/ml fentanyl citrate and 1.25 mg/ml Midazolam) 2 ml/kg as a priming dose to timepoint −35 min prior to test substance dosing and additional 1 ml/kg to timepoint −5 min prior to test substance dosing, and then 1 ml/kg every 45 minutes (4 times).

The rats were allocated into 5 groups, 6 rats in 4 groups being administrated human insulin and A21C-MM(PEG)$_{12}$ desB30 human insulin and 5 rats in a 5th group being administrated vehicle. The animals were dosed with an intravenous injection in a tail vein (1 ml/kg) of either vehicle (5 mM phosphate buffer, 140 mM NaCl, 70 ppm polysorbate 20, pH 7.4) or the derivative A21C-MM(PEG)$_{12}$ desB30 human (1.2 nmol/kg or 3.6 nmol/kg) or human insulin (1.2 nmol/kg or 3.6 nmol/kg). Blood samples for the determination of whole blood glucose concentration were collected in heparinized 10 µl glass tubes by puncture of the capillary vessels in the tail tip to time −15 min and 0 min before dosing, and to time 3, 7, 15, 30, 60, 120, 180 and 240 minutes after dosing. The blood glucose concentrations were measured after dilution in analysis buffer (500 µl) by the immobilized glucose oxidase method using a Biosen® autoanalyzer (EKF Diagnostic®, Germany).

Figure 4:
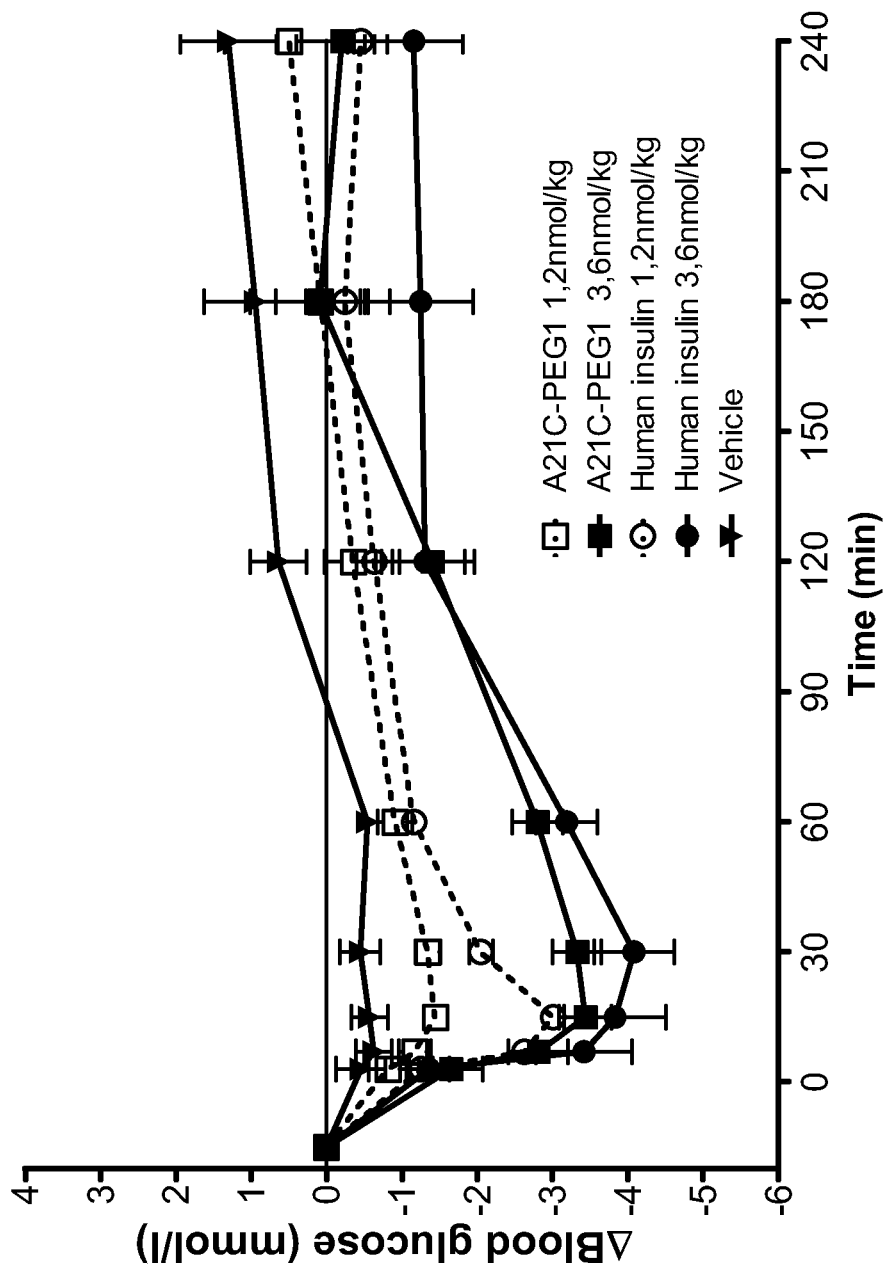
FIG. 4 shows the lowering of blood glucose level in rats following insulin analogue or human insulin intravenous injection.

The results are reported on FIG. 4, where the difference in blood glucose level (y-axis, in mmol/L) in the rats is indicated along time α-axis, in minutes) following insulin analogue or human insulin intravenous injection.

The (○) curve corresponds to 1.2 nmol/kg of human insulin, the (●) curve corresponds to 3.6 nmol/kg human insulin, the (□) curve corresponds to 1.2 nmol/kg A21C-PEG1, the (■) curve corresponds to 3.6 nmol/kg A21C-PEG1 and the (▼) curve corresponds to vehicle only. The values are the mean values from experiments repeated 5 to 6 times each.

The data show that the analogue lowers the blood glucose levels in rats, though not to the same extend as human insulin. Estimations of the mean resident time (MRT) in the plasma by ELISA showed an increase compared to human insulin from 5 min to 31 min, for the low doses. This means that the insulin derivatives of the invention present an extended half-life after administration compared to human insulin.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A human insulin analogue comprising a human insulin or a desB30 human insulin having one substitution wherein the substitution is a cysteine substitution selected from the group consisting of A10C, A14C, A15C, A18C, A19C, A21C, B25C, B27C.

2. A human insulin analogue according to claim 1, wherein the cysteine substitution is A21C.

3. A human insulin analogue according to claim 1 selected from the group consisting of A10C human insulin, A14C human insulin, A15C human insulin, A18C human insulin, A19C human insulin, A21C human insulin, B25C human insulin, B27C human insulin, A10C, desB30 human insulin, A14C, desB30 human insulin, A15C, desB30 human insulin, A18C, desB30 human insulin, A19C, desB30 human insulin, A21C, desB30 human insulin, B25C, desB30 human insulin, B27C, desB30 human insulin.

4. A human insulin derivative comprising a human insulin analogue according to claim 1 wherein the substituting cysteine is covalently attached to a methyl maleimide polyethylene glycol molecule (MM(PEG)) or to a N-ethylmaleimide molecule (NEM).

5. A human insulin derivative of claim 4 selected from the group consisting of A10C-MM(PEG)$_{12}$ human insulin, A14C-MM(PEG)$_{12}$ human insulin, A15C-MM(PEG)$_{12}$ human insulin, A18C-MM(PEG)$_{12}$ human insulin, A19C-MM(PEG)$_{12}$ human insulin, A21C-MM(PEG)$_{12}$ human insulin, B25C-MM(PEG)$_{12}$ human insulin, B27C-MM(PEG)$_{12}$ human insulin, A10C-MM(PEG)$_{12}$ desB30 human insulin, A14C-MM(PEG)$_{12}$ desB30 human insulin, A15C-MM(PEG)$_{12}$ desB30 human insulin, A18C-MM(PEG)$_{12}$ desB30 human insulin, A19C-MM(PEG)$_{12}$ desB30 human insulin, A21C-MM(PEG)$_{12}$ desB30 human insulin, B25C-MM(PEG)$_{12}$ desB30 human insulin and B27C-MM(PEG)$_{12}$ desB30 human insulin, A10C-NEM human insulin, A14C-NEM human insulin, A15C-NEM human insulin, A18C-NEM human insulin, A19C-NEM human insulin, A21C-NEM human insulin, B25C-NEM human insulin, B27C-NEM human insulin, A10C-NEM desB30 human insulin, A14C-NEM desB30 human insulin, A15C-NEM desB30 human insulin, A18C-NEM desB30 human insulin, A19C-NEM desB30 human insulin, A21C-NEM desB30 human insulin, B25C-NEM desB30 human insulin and B27C-NEM desB30 human insulin.

6. A method of preparing a human insulin analogue, said method comprising a step of culturing a host cell comprising a nucleic acid sequence encoding a precursor of a human insulin analogue as defined in claim 1.

7. The method according to claim 6, further comprising a step of converting the precursor into a mature human insulin analogue.

8. The method according to claim 7 wherein the conversion step is operated with an *Achromobacter lyticus* protease at a pH ranging from 4 to 10.

9. A method of preparing a human insulin derivative according to claim 4, said method comprising a step of attaching a MM(PEG) or NEM molecule onto a substituting cysteine of a human insulin analogue or a precursor thereof where the human insulin analogue comprises a human insulin or a desB30 human insulin having only one substitution wherein the substitution is a cysteine substitution selected from the group consisting of A10C, A14C, A15C, A18C, A19C, A21C, B25C, B27C.

10. The method according to claim 9, wherein a MM(PEG) or NEM molecule is attached to a precursor of a human insulin analogue obtained from culturing a host cell comprising a nucleic acid sequence encoding a precursor of a human insulin analogue, wherein the human insulin analogue comprises a human insulin or a desB30 human insulin having only one substitution wherein the substitution is a cysteine substitution selected from the group consisting of A10C, A14C, A15C, A18C, A19C, A21C, B25C, B27C.

11. The method according to claim 10, further comprising converting the precursor into a mature human insulin analogue, wherein the conversion step is operated with an *Achromobacter lyticus* protease at a pH ranging from 4 to 10.

12. The method according to claim 9, wherein the attachment of a MM(PEG) or NEM molecule and a reduction step are performed in a one-pot reaction.

13. A process for preparing human insulin derivatives comprising using a human insulin analogue according to claim 1 as a starting material or intermediate compound.

14. A method of treating diabetes in a subject in need thereof, said method comprising administering to said subject a therapeutically effective amount of a human insulin analogue of comprising a human insulin or a desB30 human insulin having only one cysteine substitution wherein the substitution is a cysteine substitution selected from the group consisting of A10C, A14C, A15C, A18C, A19C, A21C, B25C, and B27C or a human insulin derivative of claim 4.

* * * * *